(12) United States Patent
Ricks

(10) Patent No.: US 7,939,466 B2
(45) Date of Patent: May 10, 2011

(54) METHOD OF CROP PRODUCTION

(76) Inventor: Phillip E. Ricks, Conway, NC (US)

( * ) Notice: Subject to any disclaimer, the term of this patent is extended or adjusted under 35 U.S.C. 154(b) by 223 days.

(21) Appl. No.: 12/382,918

(22) Filed: Mar. 26, 2009

(65) Prior Publication Data

US 2009/0247405 A1 Oct. 1, 2009

Related U.S. Application Data

(60) Provisional application No. 61/064,781, filed on Mar. 26, 2008.

(51) Int. Cl.
*A01N 57/20* (2006.01)
*A01C 21/00* (2006.01)
*A01C 14/00* (2006.01)
*A01D 46/08* (2006.01)

(52) U.S. Cl. ............ 504/127; 111/118; 111/200; 56/28

(58) Field of Classification Search .................. 504/127; 111/118, 200; 56/28; 47/1.5
See application file for complete search history.

(56) References Cited

U.S. PATENT DOCUMENTS

| | | | |
|---|---|---|---|
| 4,994,102 A | 2/1991 | Yoshido et al. | |
| 5,793,035 A * | 8/1998 | Beck et al. | 250/222.1 |
| 6,277,625 B1 | 8/2001 | Huang et al. | |
| 6,451,731 B1 | 9/2002 | Agbaje et al. | |
| 2002/0111272 A1 | 8/2002 | Sheetz | |
| 2002/0172704 A1 | 11/2002 | Hsieh et al. | |
| 2005/0108798 A1 | 5/2005 | Davis | |
| 2005/0241019 A1 | 10/2005 | Davis | |
| 2006/0218663 A1 | 9/2006 | Castle et al. | |

OTHER PUBLICATIONS

Handbook Series Book 9. Cover Crops Profitably.Third edition 2007 Published by the Sustainable Agriculture Network, Beltsville, MD. http://www.sare.org/publications/covercrops/covercrops_conservation_tillage.shtml.*

* cited by examiner

*Primary Examiner* — Annette H Para
(74) *Attorney, Agent, or Firm* — Richard C. Litman

(57) ABSTRACT

The method of crop production provides an ecologically friendly method of planting and harvesting a crop. The method includes the steps of initially planting the seeds of a crop to be grown in at least one row and, following the planting, spraying a first herbicide on the at least one row and on regions of the ground adjacent the at least one row on either side thereof. Preferably, the first herbicide is an herbicide preparation for destroying glyphosate-resistant weeds. The crop is then allowed to sprout and grow without further chemical applications and, following sprouting of the crop, a second herbicide is sprayed on the ground. The second herbicide preferably contains glyphosate. Following the spraying of glyphosate, the crop is harvested and a cover crop is preferably planted.

7 Claims, 4 Drawing Sheets

METHOD OF CROP PRODUCTION

CROSS-REFERENCE TO RELATED APPLICATION

This application claims the benefit of U.S. Provisional Patent Application Ser. No. 61/064,781, filed Mar. 26, 2008.

BACKGROUND OF THE INVENTION

1. Field of the Invention

The present invention relates to an agricultural planting method, and particularly to a method of crop production that includes application of first and second herbicides at different times and in different locations during the crop production cycle.

2. Description of the Related Art

Successful cultivation of cotton requires a relatively long, frost-free period, relatively long exposure to sunshine, and a relatively moderate level of rainfall. Soil for growing cotton typically needs to be relatively heavy, although the level of nutrients in the soil does not need to be exceptional. In general, these conditions are met within the seasonally dry tropics and subtropics in the Northern and Southern hemispheres, although a large proportion of the cotton grown today is cultivated in areas with less rainfall, in which water levels are supplemented through water irrigation.

Conventional cotton production methods may cause ecological damage to the surrounding environment. For example, cotton requires a relatively large quantity of water, and as water resources diminish around the world, economies that rely on limited water supplies face difficulties and conflict, as well as potential environmental problems. Cotton, for example, has led to desertification in areas of Uzbekistan, where it is a major export. During the Soviet era, the Aral Sea was tapped for agricultural irrigation, largely for the production of cotton, and now salination is widespread.

The cotton industry relies heavily on chemicals, such as fertilizers and insecticides, although a very small number of farmers are moving towards an organic model of production, and organic cotton products are now available for purchase at limited locations. These cotton products are popular for baby clothes and diapers, for example. Under most definitions, organic products do not use genetic engineering.

Historically, in North America, one of the most economically destructive pests in cotton production has been the boll weevil. Due to the U.S. Department of Agriculture's highly successful Boll Weevil Eradication Program (BWEP), this pest has been eliminated from cotton in most of the United States. This program, along with the introduction of genetically engineered "Bt cotton" (which contains a bacteria gene that codes for a plant-produced protein that is toxic to a number of pests, such as tobacco budworm, cotton bollworm and pink bollworm), has allowed a reduction in the use of synthetic insecticides.

As noted above, cotton production relies on a relatively large quantity of water for proper growth. In addition to the pests noted above, weeds and other vegetation in the cotton fields and surrounding areas may inhibit cotton production, due to the weeds' siphoning of water from the soil. In addition to insecticides and fertilizers, cotton farmers often use herbicides in order to remove weeds and other vegetation from the cotton fields prior to the planting of the cotton. Glyphosate is the active ingredient in many common herbicides used for this purpose. However, glyphosate-resistant weeds, such as glyphosate-resistant horseweed, requires the use of other, non-glyphosate based herbicides.

Typically, cotton farmers use only a single type of herbicide, and this herbicide is applied to the field prior to the planting of cotton seeds therein. Such complete removal of vegetation can not only cause great ecological damage to the general environment, but also removes various helpful benefits provided by the vegetation, such as soil aeration and the addition of nitrogen to the soil. Thus, an agricultural method solving the aforementioned problems is desired.

SUMMARY OF THE INVENTION

The method of crop production provides an ecologically friendly method of planting and harvesting a crop, such as cotton. The method includes the steps of initially planting the seeds of a crop to be grown in at least one row and, following the planting, spraying a first herbicide on the at least one row and on regions of the ground adjacent the at least one row on either side thereof. Preferably, the first herbicide is an herbicide preparation for destroying glyphosate-resistant weeds. Alternatively, a plurality of differing herbicides may be applied at this time, depending on the needs of the user.

The crop is then allowed to sprout and grow without further chemical applications and, following sprouting of the crop, a second herbicide is sprayed on the entire ground, including regions outside the at least one row, outside the regions of the ground adjacent the at least: one row, and also on the row itself and in the previously sprayed band regions. The second herbicide preferably contains glyphosate. Alternatively, any herbicide that destroys weeds and plant life other than the crop itself may be applied.

Following the spraying of glyphosate, the crop may then be harvested. Preferably, following harvesting, a cover crop is planted in the ground. The cover crop is preferably a relatively small grain. In the next growing season, the method is preferably begun again without removal of the cover crop.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
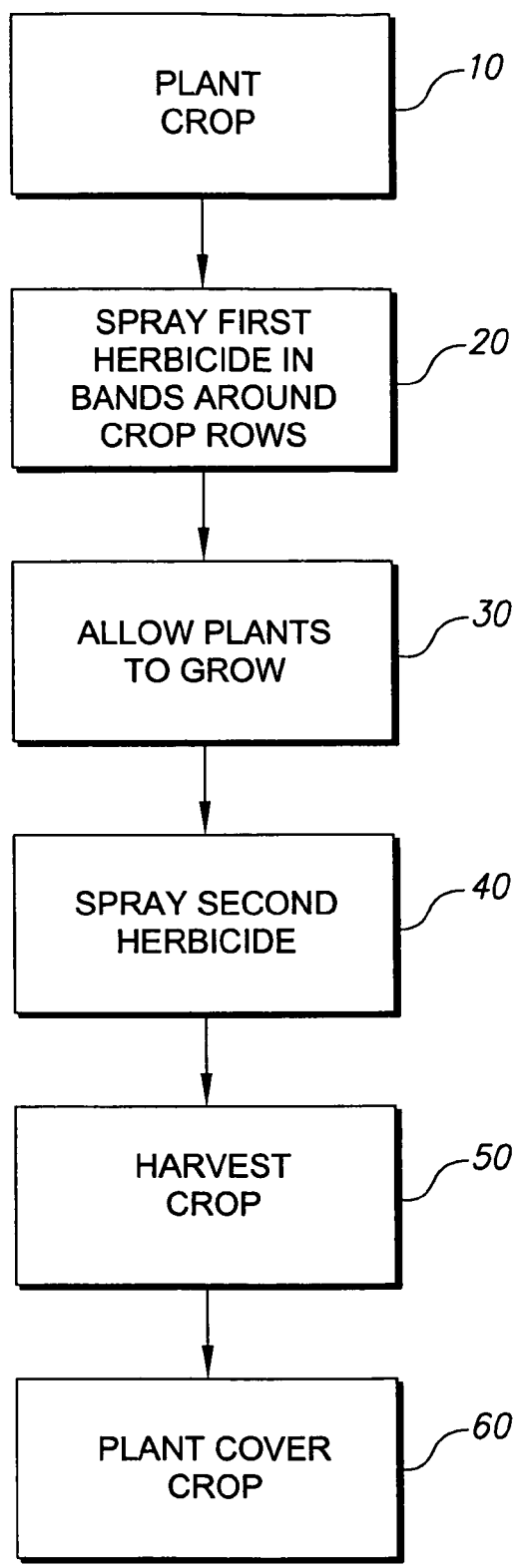
FIG. 1 is a flowchart illustrating the steps of a method of crop production according to the present invention.
Figure 2:
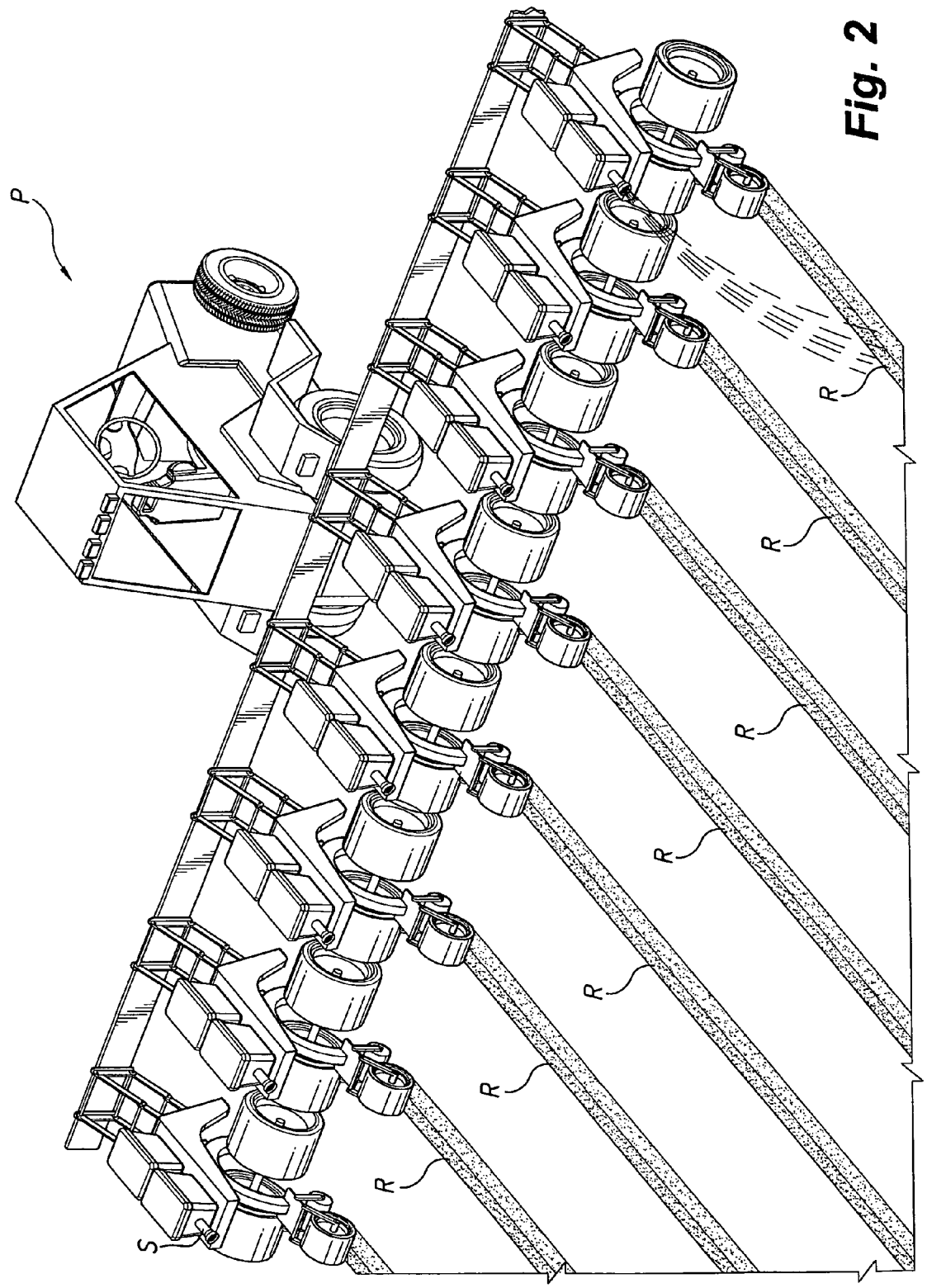
FIG. 2 is an environmental, perspective view of an exemplary planting step in the method of crop production according to the present invention.

The present invention is directed towards a method of crop production. The agricultural method provides an ecologically friendly method of planting and harvesting a crop, such as cotton. As shown in FIG. 1, the method includes the initial step of initially planting the seeds of a crop to be grown in at least one row (step 10). In FIG. 2, an exemplary cotton planter P is shown producing multiple planted rows R in the ground. It should be understood that planter P is shown for exemplary purposes only, and that the method may be used with any desired crop and any method of planting seeds in the ground, depending upon the particular crop to be grown and the conditions of the ground and general environment. Further, any desired number of rows R may be planted and formed. A sprayer (or sprayers) S is mounted to the planter P to band spray herbicide on the rows R, as will be described in detail below.

Figure 3:
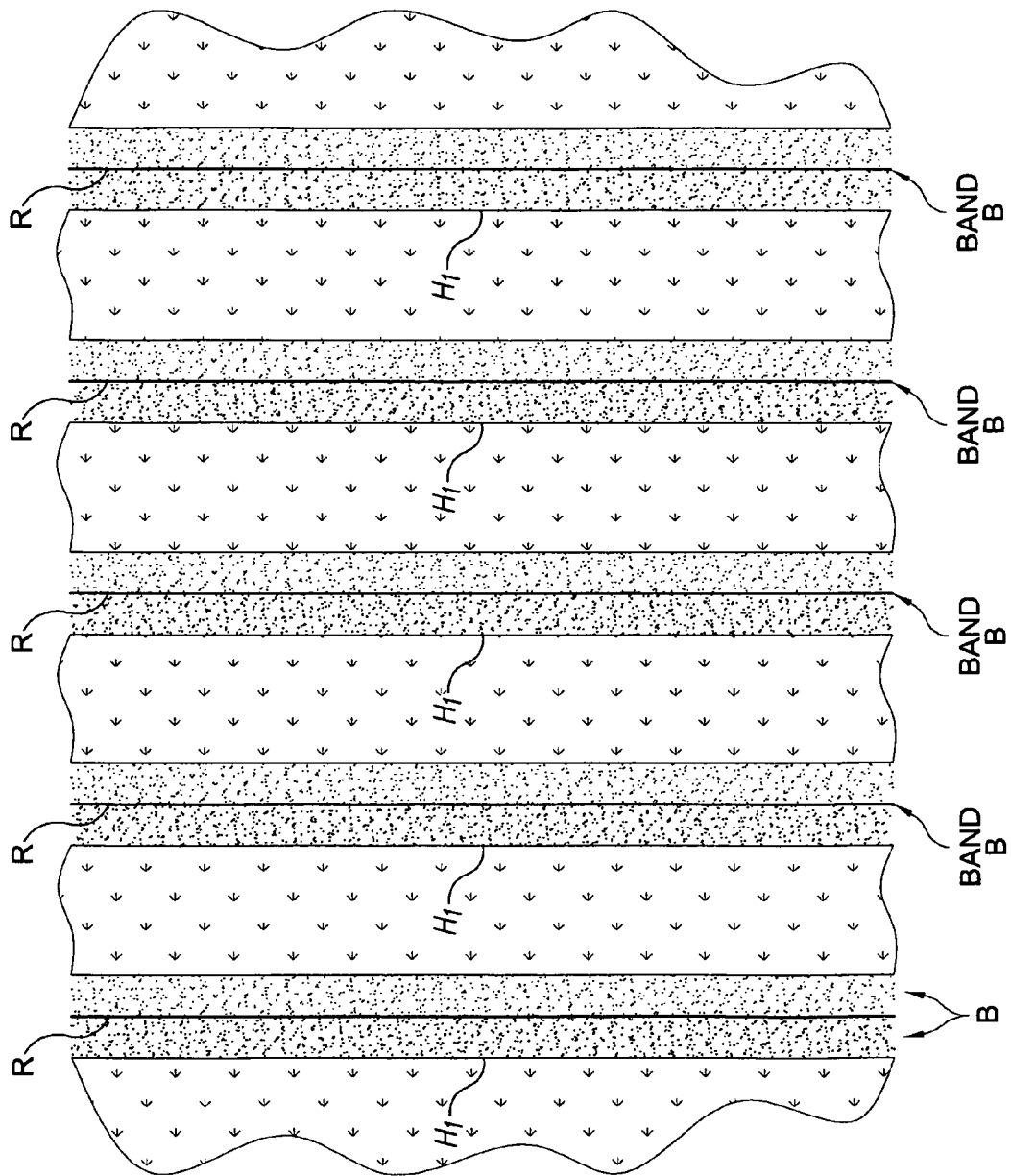
FIG. 3 is a diagrammatic view of a first spraying step in the method of crop production according to the present invention.

As shown in FIG. 3, following the planting, a first herbicide $H_1$ is sprayed on the at least one row R and on regions of the ground adjacent the at least one row R on either side thereof (step 20). The first herbicide $H_1$ is preferably sprayed in bands B about each row R, with each band B having substantially identical widths. In FIG. 3, each planted row R is illustrated as a simplified, straight line for purposes of illustration. Herbicide $H_1$ forms a band about each row R, on either side thereof, as shown. As shown, each band B extends on either side of a particular row R, and there is untreated ground between each of the bands B. As will be described in greater detail below, the rows R are not formed in soil that has been cleared of all vegetation, but are preferably formed in soil that still has a cover layer of vegetation, and the herbicide $H_1$ is applied to this vegetation. The spaces between the bands are also covered with this vegetation.

Preferably, the first herbicide $H_1$ is an herbicide preparation for destroying glyphosate resistant weeds. Glyphosate (N-(phosphonomethyl) glycine) is a non-selective systemic herbicide, which is absorbed through the leaves and used to kill weeds, especially perennial weeds. The first herbicide $H_1$ may be sprayed through the use of any suitable spraying or applicator device S, and includes an herbicidal alternative to glyphosate for destroying weeds and other vegetation that is resistant to glyphosate. As noted above, the first herbicide $H_1$ is preferably not sprayed directly on the soil, but on a layer of vegetation that has been left on the soil. Alternatively, a plurality of differing herbicides may be applied at this time, dependent on the needs of the user.

Figure 4:
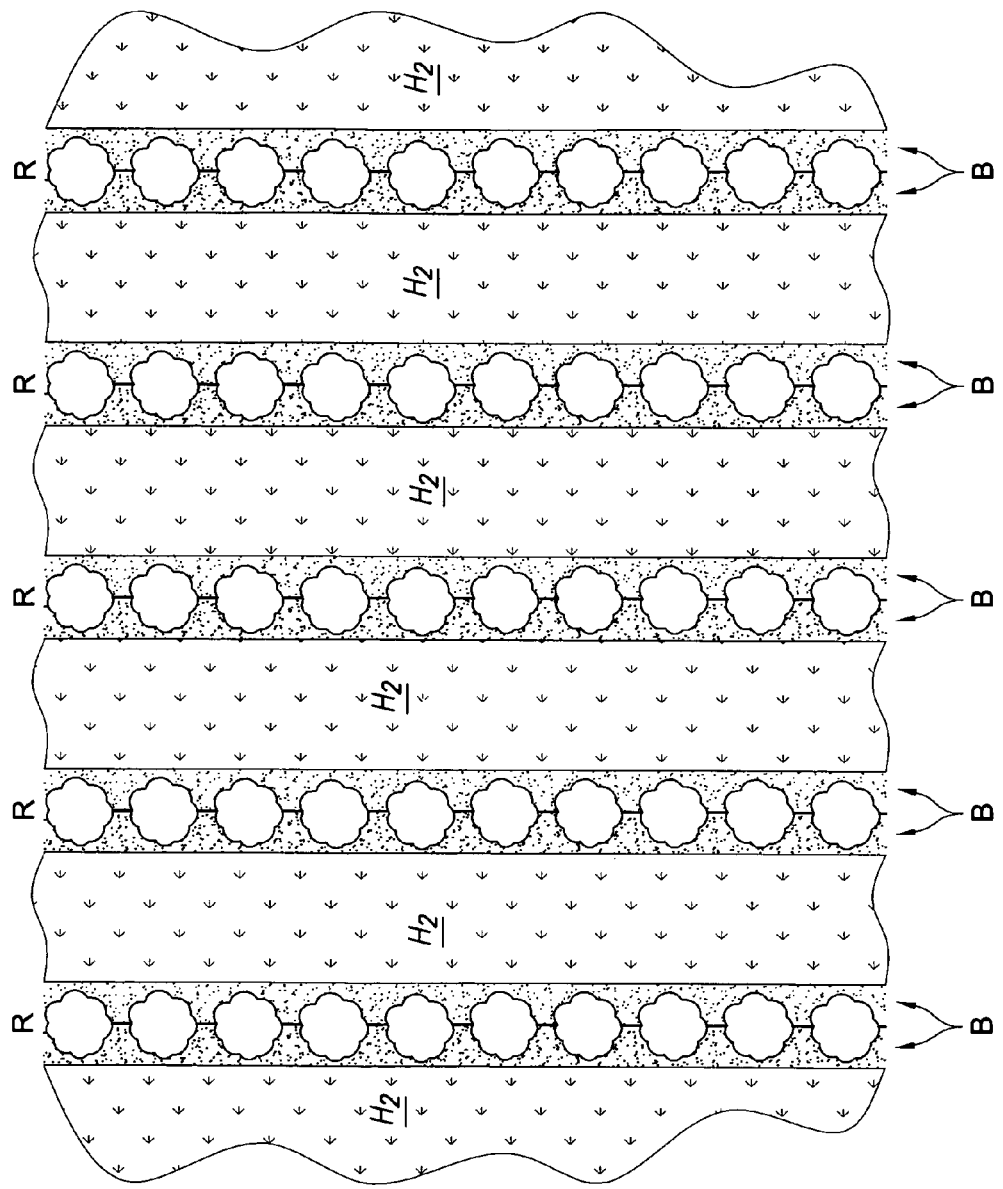
FIG. 4 is a diagrammatic view of a second spraying step in the method of crop production according to the present invention.

The crop C is then allowed to sprout and grow (step 30) without further chemical applications and, following sprouting of the crop, a second herbicide $H_2$ is sprayed on the ground, as shown in FIG. 4. It should be understood that cotton plants C are shown in FIG. 4 for exemplary purposes only. The second herbicide $H_2$ is sprayed on the entire ground, including the regions outside the at least one row R and outside the bands B, along with an overlapping region on the bands B. The second herbicide preferably contains glyphosate as an active ingredient. Alternatively, any herbicide that destroys weeds and plantlife other than the crop itself may be applied.

Following the spraying of glyphosate, the crop C may then be harvested (step 50). Preferably, following harvesting, a cover crop is planted in the field (step 60). The cover crop is preferably a relatively small grain. In the next growing season, the method is preferably begun again without removal of the cover crop. In the above, the first and second herbicides $H_1$ and $H_2$ are typically not sprayed on soil, but on the vegetation that covers the soil. This vegetation includes the cover crop planted and grown following the last harvest, as well as natural vegetation.

In conventional farming, a cover crop may be planted in order to provide protection for the soil from relatively harsh sunlight, from droughts, and from other detrimental environmental conditions. However, in conventional farming, both the cover crop and any natural vegetation, such as weeds, are removed prior to planting. In the inventive method, the cover crop and native vegetation are left on the soil throughout planting, initial growth, and up to the spraying of the glyphosate. The cover crop and vegetation improve air quality (through the natural respiration cycle of the plants, which removes carbon dioxide from the air and produces breathable oxygen), the vegetation produces seeds for birds to eat, and the vegetation aerates the soil and produces nitrogen for richer soil. Further, as the cover crop decays, it produces "crop residue", which acts as a protective cover over the soil during harsh environmental conditions.

It is to be understood that the present invention is not limited to the embodiment described above, but encompasses any and all embodiments within the scope of the following claims.

I claim:

1. A method of crop production, comprising the steps of:
    planting seeds of a crop in at least one row;
    spraying a first herbicide on the at least one row and in bands adjacent the at least one row on either side thereof;
    following sprouting of the crop, spraying a second herbicide on the ground; and
    harvesting the crop.

2. The method of crop production as recited in claim 1, wherein the step of spraying the first herbicide includes spraying an herbicide preparation formulated to remove glyphosate-resistant weeds.

3. The method of crop production as recited in claim 2, wherein the step of spraying the second herbicide includes spraying an herbicide containing glyphosate.

4. The method of crop production as recited in claim 1, further comprising the step of planting a cover crop following the step of harvesting.

5. A method of crop production, comprising the steps of:
    planting seeds of a crop in at least one row;
    spraying a first herbicide on the at least one row and in bands adjacent the at least one row on either side thereof, the first herbicide being formulated to remove glyphosate-resistant weeds;
    following sprouting of the crop, spraying a second herbicide on the ground; and
    harvesting the crop.

6. The method of crop production as recited in claim 5, wherein the step of spraying the second herbicide includes spraying an herbicide containing glyphosate.

7. The method of crop production as recited in claim 6, further comprising the step of planting a cover crop following the step of harvesting.

* * * * *